US009566470B2

(12) United States Patent
 Malizia

(10) Patent No.: US 9,566,470 B2
(45) Date of Patent: Feb. 14, 2017

(54) LEG STRETCHER

(71) Applicant: Mary Ann Malizia, Rockville Centre, NY (US)

(72) Inventor: Mary Ann Malizia, Rockville Centre, NY (US)

( * ) Notice: Subject to any disclaimer, the term of this patent is extended or adjusted under 35 U.S.C. 154(b) by 0 days.

(21) Appl. No.: 15/071,869

(22) Filed: Mar. 16, 2016

(65) Prior Publication Data

US 2016/0271443 A1 Sep. 22, 2016

Related U.S. Application Data

(60) Provisional application No. 62/177,431, filed on Mar. 16, 2015.

(51) Int. Cl.
 *A61H 1/00* (2006.01)
 *A61H 1/02* (2006.01)
 (Continued)

(52) U.S. Cl.
 CPC ........... *A63B 23/0488* (2013.01); *A61H 1/024* (2013.01); *A63B 21/4011* (2015.10);
 (Continued)

(58) Field of Classification Search
 CPC ............. A63B 21/4011; A63B 21/4013; A63B 21/4015; A63B 23/0482; A63B 23/0488; A63B 23/0494; A63B 2023/006; A63B 23/2023; A63B 23/006; A63B 24/0087; A61H 1/0237; A61H 1/0244; A61H 1/024; A61H 2201/0142; A61H 2201/0207; A61H 2201/0214; A61H 2201/0257; A61H 2201/10; A61H 2201/1215; A61H 2201/1642; A61H 2201/1676; A61H 2201/50; A61H 2201/5069; A61H 2201/5097
 See application file for complete search history.

(56) References Cited

U.S. PATENT DOCUMENTS 4,089,330 A * 5/1978 Nicolosi .................. A61H 1/02
 601/33
4,226,415 A * 10/1980 Wright ............. A63B 23/03525
 482/113
(Continued)

FOREIGN PATENT DOCUMENTS

KR 20110017047 A 2/2011

OTHER PUBLICATIONS

The International Search Report PCT/US16/22624 dated May 23, 2016.

*Primary Examiner* — Joshua Lee
(74) *Attorney, Agent, or Firm* — Carter, DeLuca, Farrell & Schmidt, LLP

(57) ABSTRACT

A leg stretching device includes a base frame, a support plate adjustably coupled to the base frame, a leg tube including a proximal end hingedly connected to the base frame and a distal end, a foot plate disposed at the distal end of the leg tube, and an actuation assembly including an actuation tube hingedly connected to the base frame and an actuation bar slidably disposed within the actuation tube and hingedly connected to the leg tube. The actuation assembly includes an actuator motor for moving the actuation bar relative to the actuation tube to reposition the leg tube relative to the base frame.

18 Claims, 7 Drawing Sheets

(51) Int. Cl.
*A61H 5/00* (2006.01)
*A63B 21/002* (2006.01)
*A63B 21/00* (2006.01)
*A63B 23/04* (2006.01)
*A63B 23/00* (2006.01)
*A63B 24/00* (2006.01)
*A61N 1/00* (2006.01)
*A61N 1/36* (2006.01)

(52) U.S. Cl.
CPC ........... *A61H 2201/0142* (2013.01); *A61H 2201/0207* (2013.01); *A61H 2201/0214* (2013.01); *A61H 2201/0257* (2013.01); *A61H 2201/10* (2013.01); *A61H 2201/1215* (2013.01); *A61H 2201/1642* (2013.01); *A61H 2201/1676* (2013.01); *A61H 2201/50* (2013.01); *A61H 2201/5069* (2013.01); *A61H 2201/5097* (2013.01); *A61N 1/00* (2013.01); *A61N 1/36003* (2013.01); *A63B 21/4013* (2015.10); *A63B 21/4015* (2015.10); *A63B 24/0087* (2013.01); *A63B 2023/006* (2013.01)

(56) References Cited

U.S. PATENT DOCUMENTS

| | | | | |
|---|---|---|---|---|
| 4,558,692 A | * | 12/1985 | Greiner | A61H 1/0255 601/33 |
| 4,647,040 A | * | 3/1987 | Ehrenfried | A61H 1/02 482/131 |
| 4,802,462 A | | 2/1989 | Reiss et al. | |
| 4,905,677 A | * | 3/1990 | Pecheux | A61H 1/0259 601/33 |
| 5,122,106 A | * | 6/1992 | Atwood | A61H 1/0244 482/131 |
| 5,163,890 A | | 11/1992 | Perry, Jr. | |
| 5,232,427 A | | 8/1993 | Paro | |
| 5,236,333 A | * | 8/1993 | Barba, Jr. | A61H 1/024 482/125 |
| 5,277,681 A | * | 1/1994 | Holt | A61H 1/02 482/112 |
| 5,328,426 A | * | 7/1994 | Vendette | A63B 23/0482 482/39 |
| 5,333,604 A | * | 8/1994 | Green | A61H 1/0255 601/33 |
| 5,421,801 A | * | 6/1995 | Davies, III | A61H 1/0244 482/131 |
| 5,460,596 A | * | 10/1995 | Brady | A61H 1/0244 482/79 |
| 5,498,222 A | | 3/1996 | Hur | |
| 5,662,562 A | * | 9/1997 | Wohlenberg | A61H 1/024 482/907 |
| 5,662,592 A | * | 9/1997 | Brady | A63B 23/04 482/139 |
| 5,901,581 A | * | 5/1999 | Chen | A61H 1/0259 601/33 |
| 5,913,759 A | * | 6/1999 | Bostrom | A61H 1/0255 482/131 |
| 7,014,602 B2 | * | 3/2006 | Yamauchi | A61H 1/0218 482/142 |
| 7,235,039 B2 | * | 6/2007 | Anders | A61H 1/0218 482/51 |
| 7,476,182 B2 | * | 1/2009 | DeNisco | A61H 1/0244 482/907 |
| 7,556,594 B2 | | 7/2009 | Houston | |
| 7,604,583 B2 | * | 10/2009 | Denisco | A61H 1/0244 482/142 |
| 7,762,936 B2 | | 7/2010 | Conley et al. | |
| 8,267,843 B2 | * | 9/2012 | Dellino | A63B 21/0615 482/100 |
| 9,358,174 B1 | * | 6/2016 | Gallo | A61H 1/0292 |
| 2002/0193710 A1 | | 12/2002 | Main et al. | |
| 2004/0157712 A1 | * | 8/2004 | Bodily | A61H 1/0266 482/142 |
| 2006/0142130 A1 | * | 6/2006 | Nichols | A61H 1/02 482/139 |
| 2008/0182730 A1 | * | 7/2008 | Conley | A61H 1/0244 482/95 |
| 2008/0227610 A1 | * | 9/2008 | Chen | A61H 1/0218 482/143 |
| 2009/0093353 A1 | * | 4/2009 | Weiner | A61H 1/024 482/130 |
| 2010/0313897 A1 | * | 12/2010 | Schaeffer | A61H 1/0222 128/845 |
| 2013/0225378 A1 | * | 8/2013 | Burek | A63B 26/00 482/142 |
| 2014/0194266 A1 | * | 7/2014 | Raiten | A63B 23/0482 482/142 |

* cited by examiner

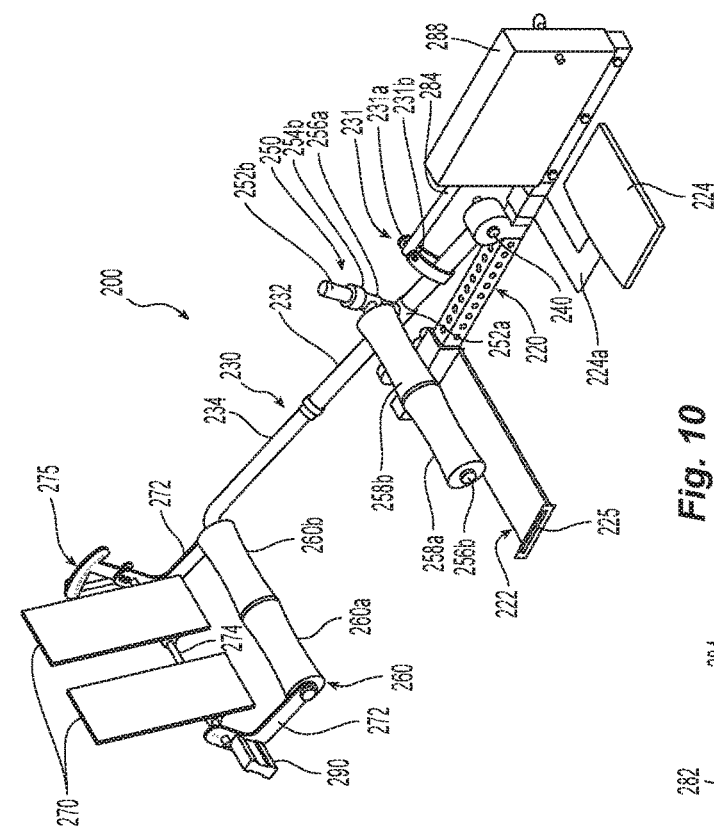
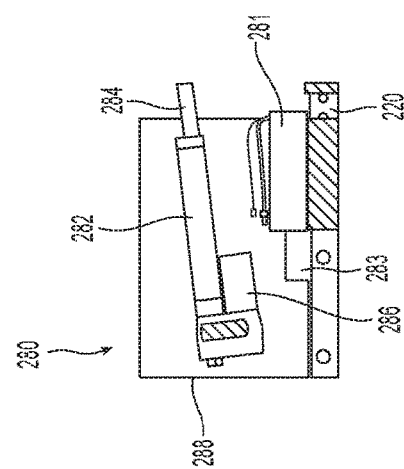
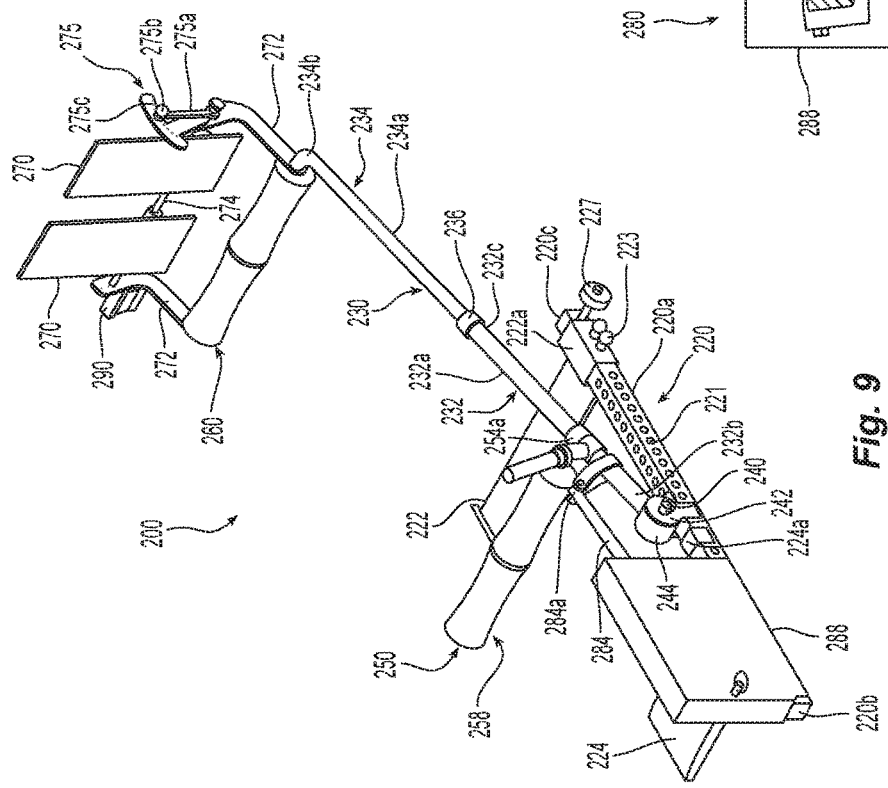

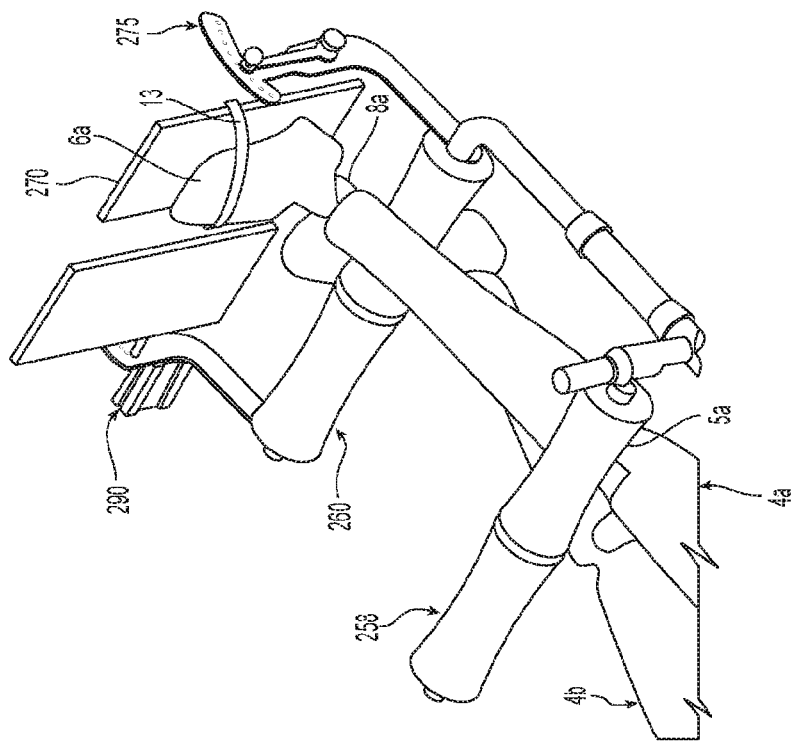
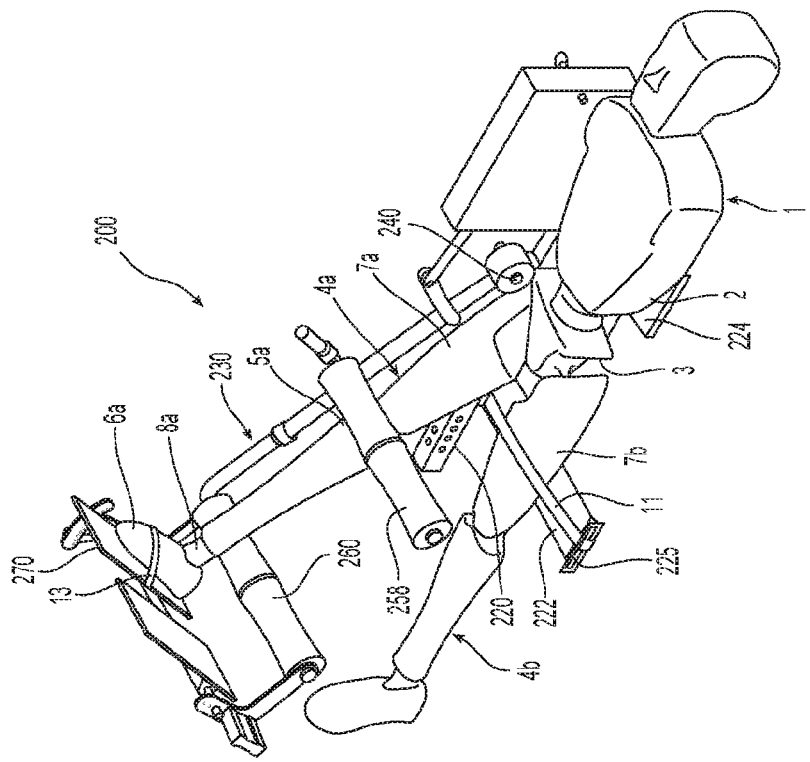

LEG STRETCHER

CROSS-REFERENCE TO RELATED APPLICATIONS

The present application claims priority to, and the benefit of U.S. Provisional Patent Application Ser. No. 62/177,431, filed on Mar. 16, 2015, the entire contents of which are hereby incorporated by reference herein.

BACKGROUND

Technical Field

The present disclosure relates to muscle stretching devices and methods of using the stretching devices for stretching muscles of a leg of user, and in particular, devices and methods of stretching hamstring and/or gastrocnemius muscles of a user.

Background of Related Art

Stretching of the body is performed for a variety of reasons, including, for example, decreasing muscle tone, increasing range of motion, improving flexibility, decreasing pain, and/or preventing injury. Equipment has been developed to aid in stretching different parts of the body, such as the arms and legs. Examples of devices for leg stretching are described in: U.S. Pat. No. 4,226,415, which relates to a "Universal Exercise Apparatus for Performing Hamstring Flex and Other Exercises;" U.S. Pat. No. 5,232,427, which relates to a "Leg Stretching Apparatus;" U.S. Pat. No. 5,498,222, which relates to an "Exercise Device;" U.S. Pat. No. 5,913,759, which relates to a "Stretching Apparatus;" U.S. Pat. No. 7,476,182, which relates to a "Horizontal Hamstring Stretcher;" U.S. Pat. No. 7,762,936, which relates to a "Stretching and Conditioning Apparatus;" U.S. Patent Appl. Pub. No. 2002/0193710, which relates to a "Leg Stretching Apparatus;" and Korean Patent Pub. KR 2011/0017047, which relates to an "Apparatus For Evaluation Hamstring Tightness Or Flexibility And Method Thereof."

SUMMARY

In one aspect of the present disclosure, a leg stretching device includes a base frame, a support plate adjustably coupled to the base frame, a leg tube including a proximal end hingedly connected to the base frame and a distal end, a foot plate disposed at the distal end of the leg tube, and an actuation assembly including an actuation tube hingedly connected to the base frame and an actuation bar slidably disposed within the actuation tube and hingedly connected to the leg tube. The actuation assembly includes an actuator motor for moving the actuation bar relative to the actuation tube to raise or lower the leg tube relative to the base frame.

The leg stretching device may further include a lower lumbar pad adjustably coupled to the base frame. In some embodiments, the lower lumbar pad is connected to the support plate by at least one lumbar support pad adjustment strap.

The leg stretching device may further include a thigh foam support roller and/or a foam ankle cuff roller adjustably coupled to the leg tube.

The leg tube may be hingedly connected to the base frame about a pivot axle. In some embodiments, the pivot axle extends through a hinge cover, and the hinge cover includes a degree label.

The leg tube may include an upper leg tube telescopically coupled with a lower leg tube so that the overall length of the leg tube is adjustable. In embodiments, a thigh foam support roller includes a thigh pad disposed around a thigh support axle extending from a thigh support adjustment bracket, and the upper leg tube includes a plurality of adjustment holes defined therethrough that are dimensioned to receive the thigh support adjustment bracket for securing the thigh foam support roller to the upper leg tube. In some embodiments, a foam ankle cuff roller includes an ankle pad disposed around an ankle support axle extending from an ankle support bracket, and the lower leg tube includes an ankle axle support hole dimensioned to receive the ankle support bracket for securing the foam ankle cuff roller to the lower leg tube. In certain embodiments, the footplate includes footplate support axles extending into position holes of a footplate adjustment bracket, and the footplate adjustment bracket is secured to the lower leg tube.

The leg stretching device may include an electronic controller for controlling the actuator motor of the actuation assembly. In some embodiments, the electronic controller is a handheld remote control.

In another aspect of the present disclosure, a method of stretching a leg includes: resting a torso of a user on a support plate that is adjustably coupled to a base frame of a leg stretching device; aligning a hip of the user with a hip pivot axle of the leg stretching device, the hip pivot axle hingedly connecting the base frame of the leg stretching device to a leg tube of the leg stretching device; resting a foot of the user against a footplate disposed at a distal end of the leg tube of the leg stretching device; and actuating an actuator motor of the leg stretching device to raise the leg tube and elevate the foot of the user.

The method may further include resting a lower back of the user against a lower lumbar pad that is adjustably coupled to the base frame of the leg stretching device.

In embodiments, the method includes resting a knee of the user against a thigh foam support roller of the leg stretching device, the thigh foam support roller being adjustably coupled to the leg tube of the leg stretching device.

In some embodiments, the method includes resting an ankle of the user against a foam ankle cuff roller of the leg stretching device, the foam ankle cuff roller being adjustably coupled to the leg tube of the leg stretching device.

The method may further include strapping at least one of a thigh, an ankle, or a foot of the user to the leg stretching device with a retention strap.

The method may further include adjusting a position of at least one of the support plate or the footplate prior to actuating the actuator motor.

In embodiments, the method includes measuring a degree of hip flexion at the hip pivot axle.

The leg stretching device of the present disclosure is free-standing and portable. The user is not restricted to use the device in a pre-installed location, and may transport and use the device in a variety of places.

The leg stretching device of the present disclosure includes a number of adjustment members for tailoring the stretching device to accommodate various body types. The leg stretching device includes a number of adjustment knobs that interface with adjustable structural members for the purpose of accommodating various body sizes and/or shapes. For example, in embodiments, a lower leg tube adjustment knob allows the user to adjust the length of a lower leg tube to accommodate various leg lengths. As another example, in embodiments, a footplate is adjustable by the alignment and securement of the footplate with a footplate support adjustment knob.

The leg stretching device of the present disclosure includes a number of structural elements for the purpose of stabilizing the device by using the user's own weight during use. For example, in embodiments, the leg stretching device includes a support plate and/or lumbar support pad on which a user lies to stabilize the device.

In embodiments, the leg stretching device of the present disclosure allows a user to stretch a number of different muscles. For example, raising and lowering the leg allows the user to stretch the hamstring and the calf of the user. As another example, the user may lie on their stomach and stretch the hip flexor muscles.

In embodiments, the leg stretching device includes foam supports and/or retention straps for the purpose of stabilizing the knee, the ankle, and/or the foot of the user to maintain the leg in correct mechanical alignment in the most lengthened position of the muscle for maximum stretching efficacy of the hamstring and calf muscles.

Other aspects, features, and advantages will be apparent from the description, drawings, and the claims.

BRIEF DESCRIPTION OF THE DRAWINGS

FIGS. 9 and 10 are side perspective views of a leg stretch device in accordance with yet another embodiment of the present disclosure;

FIG. 11 is a side view of an actuation assembly of the leg stretch device of FIGS. 9 and 10 with a portion of a housing of the actuation assembly removed;

FIG. 12A is side perspective view of the leg stretch device of FIGS. 9 and 10 in use by a human user; and FIG. 12B is an enlarged perspective view of a distal end of the leg stretch device and the human user of FIG. 12A.

Corresponding reference characters indicate corresponding parts throughout the drawings.

DETAILED DESCRIPTION

Figure 1:
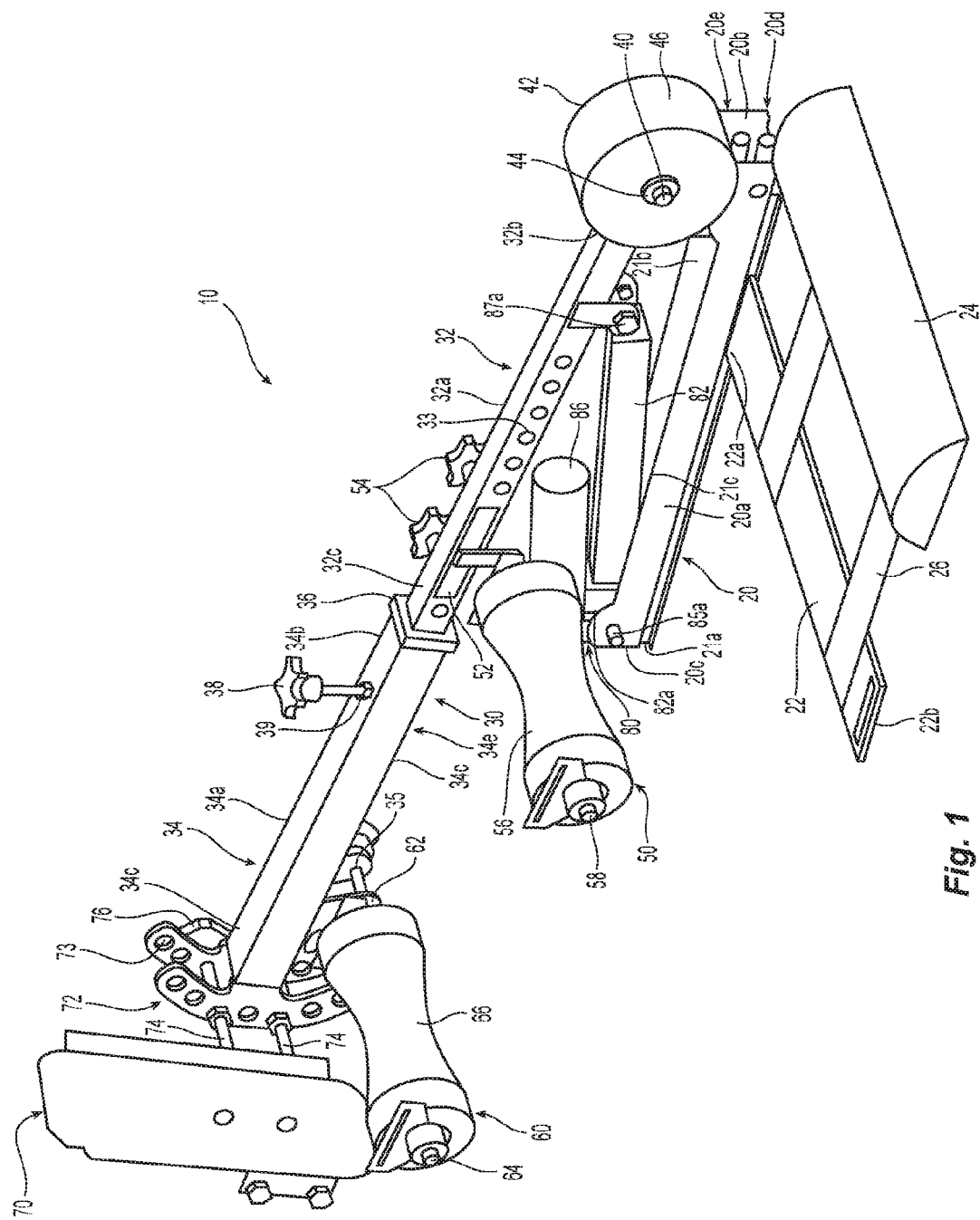
FIG. 1 is a side perspective view of a leg stretch device in accordance with an embodiment of the present disclosure in an initial elevation position.
Figure 2:
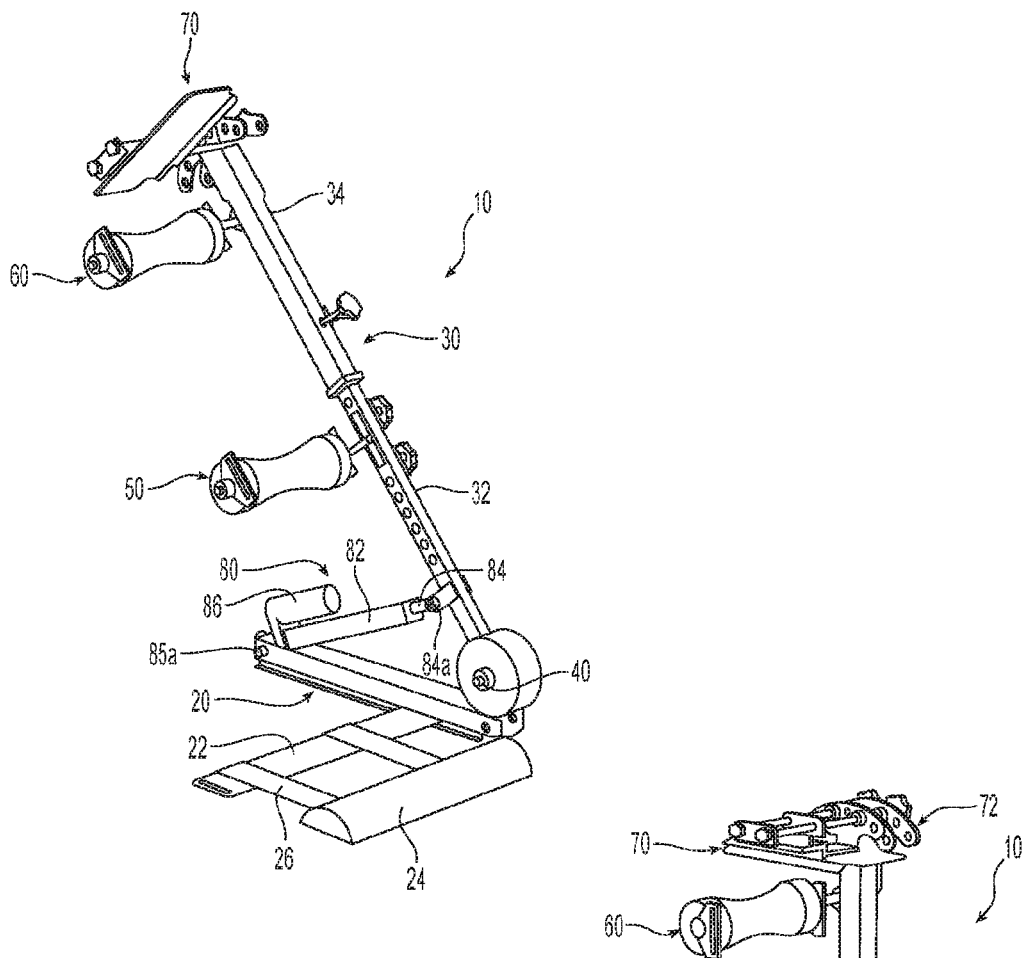
FIG. 2 is a side perspective view of the leg stretch device of FIG. 1 positioned in an increased elevation position.
Figure 3:
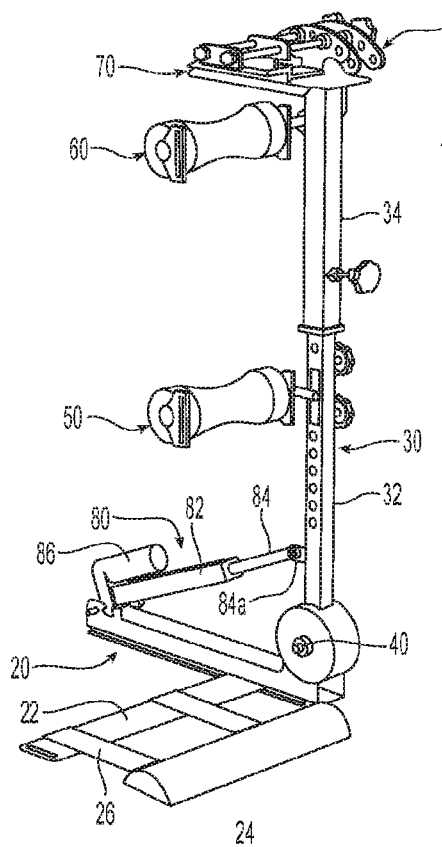
FIG. 3 is a side perspective view of the leg stretch device of FIGS. 1 and 2 positioned in a further increased elevation position.

The leg stretch device of the present disclosure stretches a hamstring of a user by elevating a leg of the user in a controlled manner by actuating a controllable motor by way of an electronic controller, such as a handheld remote control. The leg of the user is coupled to leg tube(s) of the leg stretch device and held in place by a thigh foam support roller, a foam ankle cuff roller, and/or a footplate, such that the leg is straight and the muscles are in the most lengthened position, and then the leg is elevated by the controllable motor. The controlled elevation and descent of the leg provides a controlled stretching of the hamstring, calf, and hip flexor muscles, and the leg stretch device also provides a method for stretching the hamstring muscles of the user.

Devices and methods of the present disclosure may be utilized for home and/or clinical use (e.g., physical therapy offices, chiropractic practice, health clubs, school athletic facilities, etc.), and has a range of applications (e.g., muscle shortening, tightness, and contractures, injury prevention and recovery, treatment of various orthopedic and neurological disorders such as knee contractures, status post knee, ankle and hip surgeries/sprains/strains, cerebral palsy, spinal cord injuries, Parkinson's disease, multiple sclerosis, and restless leg syndrome, etc.). It should be understood that while the devices and methods of the present disclosure are described for stretching of hamstring, calf, and hip flexor muscles, other applications are additionally or alternatively possible. For example, it should be appreciated that devices and methods of the present disclosure may be used in a range of muscle stretching applications including, for example, stretching of muscles of the hip flexors/extensors/adductors, hamstring, calf, ankle, and/or foot.

In this disclosure, the term "proximal" refers to the portion of a structure closer to a user, while the term "distal" refers to the portion of the same structure further from the user. As used herein, the term "user" refers to a human. The term "clinician" refers to a doctor, nurse, physical therapist, chiropractor, athletic trainer, or other care provider, and may include support personnel. The terms "generally," "substantially," and "about" shall be understood as words of approximation that take into account relatively little to no variation in the modified term(s) (e.g., differing by less than 10%). Additionally, in the drawings and in the description that follows, terms such as upper, lower, top, bottom, and similar directional terms are used simply for convenience of description and are not intended to limit the disclosure.

Referring now to FIGS. 1-4, a leg stretch device 10 includes an actuator leg lift tube frame or base frame 20 positionable against a support surface, such as a floor or table. The base frame 20 includes an elongated body 20a having a proximal end 20b and a distal end 20c. A recess 21a is defined within a lower portion 20d of the base frame 20, and extends along the length of the base frame 20. The recess 21a is dimensioned to receive a first end 22a of a swivel base support plate 22. The support plate 22 is slidable along the longitudinal length of the base frame 20 and extends substantially perpendicularly from the base frame 20 and terminates at a second end 22b. It should be understood that the recess 21a may extend through the base frame 20 so that the support plate 22 may be pivoted to the opposed side of the base frame 20 for stretching of either a left leg or a right leg of a user, or a second recess (not shown) may be disposed in the lower portion 20d of the base frame 20 in a position opposite the recess 21a so that the support plate 22 may be moved to the opposed side of the base frame 20 for stretching of either the left or right leg of the user.

The support plate 22 is coupled to a lower lumbar pad 24 by one or more lumbar support pad adjustment straps 26. The placement of the lower lumbar pad 24 with respect to the support plate 22 may be adjusted to accommodate the height and/or body proportion of a user. In embodiments, the lower lumbar pad 24 is a half-moon shaped pad for supporting the lower back of a user. It should be understood that the lower lumbar pad 24 may be any pelvic arch support pillow or pad in a variety of sizes and shapes for supporting a user's lower back, and that the leg stretch device 10 of the present disclosure may include a plurality of different sized and/or shaped lower lumbar pads for interchangeable use depending on the size and needs of the user.

A leg frame 30 is coupled to the base frame 20. The leg frame 30 includes an upper leg tube 32 slidably coupled or telescopically mated with a lower leg tube 34. The upper leg tube 32 is hingedly connected to the proximal end 20b of the base frame 20 at hip pivot axle 40 such that the upper and lower leg tubes 32 and 34 move relative to the base frame 20 about a pivot axis defined by the hip pivot axle 40.

The hip pivot axle 40 extends through a hinge cover 42 and includes retaining collars 44 disposed at terminal ends of the hip pivot axle 40. The hinge cover 42 aids in preventing articles, such as body parts and clothing, from being injured and/or interfering with proper operation of the leg stretch device 10 during movement of the upper leg tube 32 relative to the base frame 20. Hinge cover 42 includes a degree label 46 and acts as a goniometer to measure the degree of hip flexion with a straight knee during use of the leg stretch device 10. Alternatively, the hinge cover 42 may include a microchip for electronic measurement and readout of the degree angle between the base frame 20 and the upper leg tube 32.

The upper leg tube 32 includes an elongated body 32a having a proximal end 32b and a distal end 32c. A plurality of adjustment holes 33 are defined through the elongated body 32a of the upper leg tube 32. The adjustment holes 33 are dimensioned to receive a thigh support adjustment bracket 52 which supports a thigh foam support roller 50, and thigh support adjustment knobs 54 for securing the thigh support adjustment bracket 52 to the upper leg tube 32. The thigh foam support roller 50 includes a thigh pad 56 disposed around a thigh support axle 58 extending from the thigh support adjustment bracket 52. It should be understood that the thigh pad 56 may be any shape and size for supporting a user's thigh or knee, and that the leg stretch device 10 of the present disclosure may include a plurality of different sized and/or shaped thigh foam support rollers 50 for interchangeable use depending on the size and needs of the user. The position of the thigh foam support roller 50 may be adjusted along the length of the upper leg tube 32 to accommodate the height and/or proportion of a user and for desired placement along the user's leg, and may be coupled to either side of the upper leg tube 32 for stretching of either a left leg or a right leg of a user.

The lower leg tube 34 includes an elongated body 34a having a proximal end 34b and a distal end 34c. The lower leg tube 34 defines an inner cavity in which a plastic telescoping sleeve 36 is disposed. It should be understood that the telescoping sleeve may be formed from other materials (e.g., aluminum, steel, polymers, other metals or alloys, etc.) that permit axial movement of the lower leg tube 34 relative to the upper leg tube 32, as is within the purview of those skilled in the art, The proximal end 34b of the lower leg tube 34 receives the distal end 32c of the upper leg tube 32 for telescopic adjustment of the lower leg tube 34 relative to the upper leg tube 32. The lower leg tube 34 is manually adjustable and secured at a desired position by a lower leg tube adjustment knob 38 having a threaded knob nut 39 to accommodate the leg length of a user.

A foam ankle cuff roller 60 is secured to the lower leg tube 34 by an ankle support bracket 62. The ankle support bracket 62 includes an ankle support axle 64 that extends into and is secured within an ankle axle support hole 35 defined in a lower surface 34e of the elongated body 34a of the lower leg tube 34. The foam ankle cuff roller 60 includes an ankle pad 66 disposed around the ankle support axle 64. It should be understood that the ankle pad 66 may be any shape and size for supporting a user's ankle, and that the leg stretch device 10 of the present disclosure may include a plurality of different sized and/or shaped foam ankle cuff rollers 60 for interchangeable use depending on the size and needs of the user. The position of the foam ankle cuff roller 60 may be adjusted by sliding the lower leg tube 34 relative to the upper leg tube 32, as described above, to accommodate the height and/or proportion of a user, and may be coupled to either side of the lower leg tube 34 for stretching of either a left leg or a right leg of a user.

A footplate 70 for supporting a foot of a user is secured to the lower leg tube 34 by a footplate adjustment bracket 72. The footplate adjustment bracket 72 is secured to the distal end 34c of the lower leg tube 34 and includes a plurality of position holes 73 through which foot support axles 74, which support the footplate 70, extend through and are secured via a footplate support adjustment knob 76. The footplate 70 may be positioned at a substantially perpendicular angle with respect to an ankle of a user (see e.g., FIG. 4), or the footplate 70 may be positioned for dorsiflexion or plantar flexion positioning of the foot by pivoting the footplate 70 about the foot support axles 74 and/or adjusting the position of the footplate 70 with respect to the position holes 73. It should be understood that the footplate 70 may be coupled to either side of the lower leg tube 34 for stretching of either a left leg or a right leg of a user by switching the sides on which the foot support axles 74 and the footplate support adjustment knob 76 extend from the footplate adjustment bracket 72.

An actuation assembly 80 is coupled to the base frame 20 and the upper leg tube 32 to effect articulation of the leg frame 30 relative to the base frame 20. The actuation assembly 80 includes an actuator tube 82 and an actuator bar 84 (see e.g., FIGS. 2 and 3) that is slidably disposed within the actuator tube 82 and controlled by an actuator motor 86. The actuator tube 82 is sized and dimensioned to be received within a cavity 21b defined in an upper portion 20e of the base frame 20. The actuator tube 82 includes a distal end 82a hingedly connected to the distal end 20c of the base frame 20 by a distal pin or rod 85a extending through a distal base frame actuator pivot hole so that the actuation assembly 80 moves relative to the base frame 20 about a pivot axis defined by the distal pin 85a. The actuator bar 84 includes a proximal end 84a (see e.g., FIGS. 2 and 3) hingedly connected to the upper leg tube 32 by a proximal pin or rod 87a extending through a proximal base frame actuator pivot hole so that the actuation assembly 80 moves relative to the upper leg tube 32 about a pivot axis defined by the proximal pin 87a. The actuator bar 84 acts as a push/pull rod for moving the leg frame 30 relative to the base frame 20 through a range of motion, such as the initial elevation position of FIG. 1 to the increased elevation positions of FIGS. 2 and 3. The increased elevation positions mimic a straight leg extension raise. It should be understood that raising and lowering of the leg frame 30 causes a corresponding raising and lowering of a user's leg, and that the user's leg may be moved to any position ranging from about 0° to about 105° relative to the base frame 20.

Figure 4:
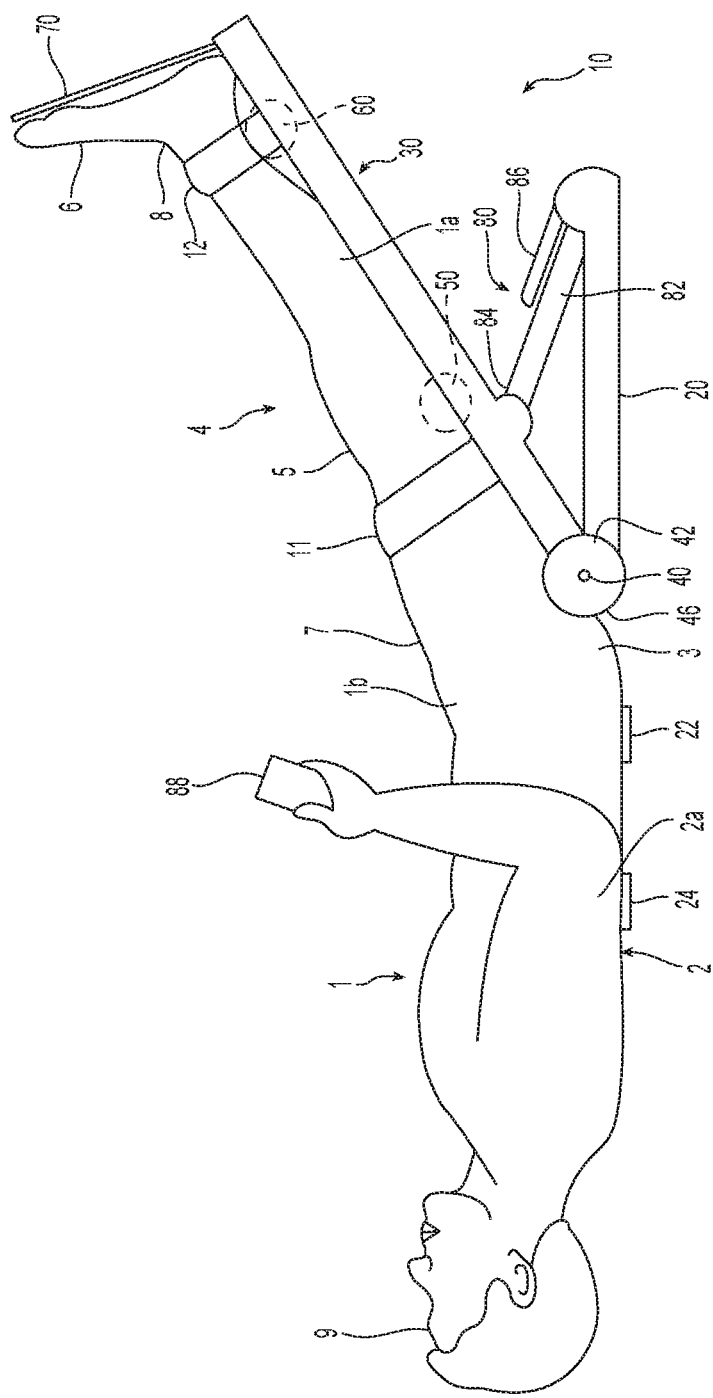
FIG. 4 is a side view of the leg stretch device of FIGS. 1-3 in use by a human user.
Figure 5:
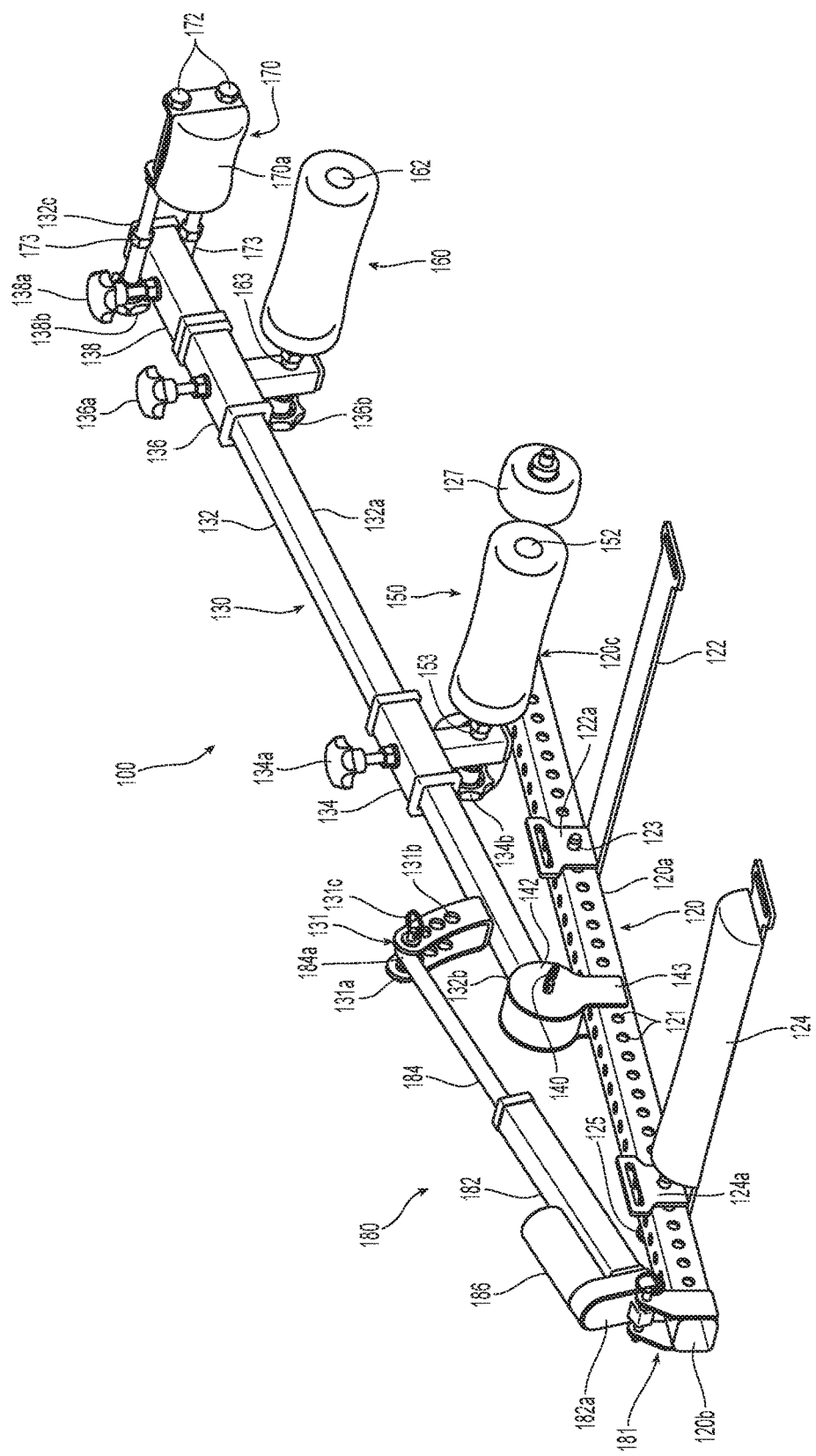
FIG. 5 is a side perspective view of a leg stretch device in accordance with another embodiment of the present disclosure.
Figure 6:
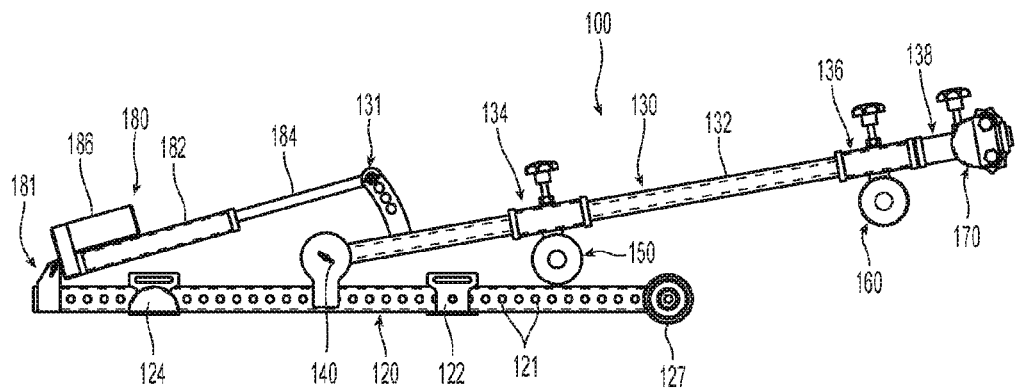
FIG. 6 is a side view of the leg stretch device of FIG. 5.
Figure 7:
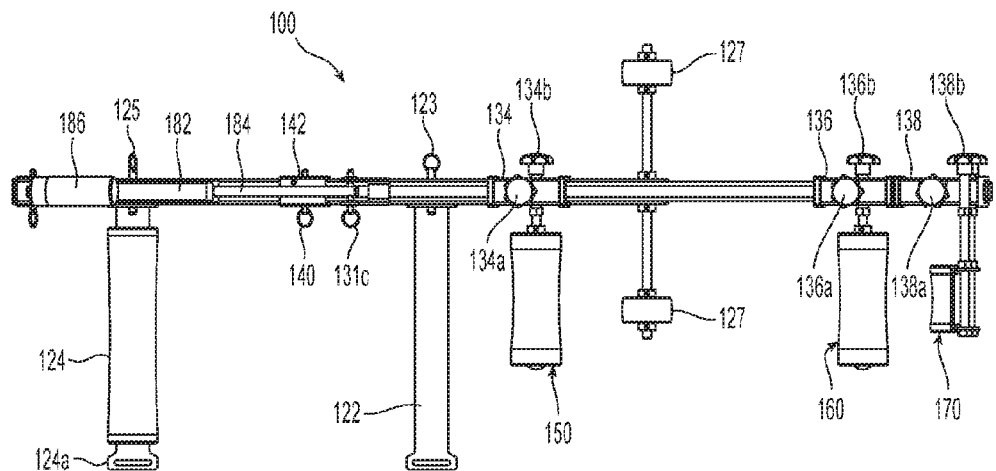
FIG. 7 is a top view of the leg stretch device of FIGS. 5 and 6.
Figure 8:
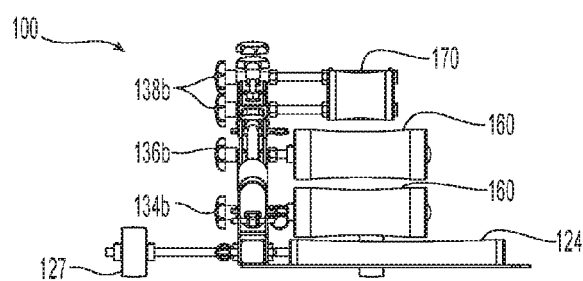
FIG. 8 is an end view of the leg stretch device of FIGS. 5-7.

The actuator motor 86 is controlled by a user or a clinician via an electronic controller 88 (FIG. 4). In embodiments, the electronic controller 88 is a handheld remote control including up and down buttons (not shown). The electronic controller 88 is in operative communication with the actuator motor 86 such that actuation of the electronic controller 88 by the user or the clinician actuates the actuator motor 86 which, in turn, causes the actuator bar 84 to slide relative to the actuator tube 82 to push or release the upper leg tube 32 to change the degree angle between the base frame 20 and the upper leg tube 32. The electronic controller 88 may be configured to communicate with the actuation motor 86 via a wireless (e.g., radio frequency, optical, WiFi, Bluetooth®, LTE, etc.) and/or wired connection. The electronic controller 88 may be programmable and include built-in programs a user may select (e.g., pre-programmed range of motion over a pre-programmed period of time).

As shown in FIG. 4, in use, a user 1 lies with the back of the user's torso 2 resting on the support plate 22, and the user's lower back 2*a* resting against the lower lumbar pad 24. The user's hip 3 is aligned with the hip pivot axle 40 so that the degree label 46 on the hinge cover 42 acts a goniometer to determine the user's range of motion. The user's leg 4 is aligned with the leg frame 30 such that the thigh foam support roller 50 presses against the thigh 7 to keep the knee 5 straight, the user's ankle 8 rests against the foam ankle cuff roller 60, and the user's foot 6 is placed against the footplate 70. As described above, the support plate 22 may be adjusted by sliding the support plate 22 relative to the base frame 20 during positioning of a user's hip 3 with the hip pivot axle 40, the lower lumbar pad 24 may be adjusted relative to the support plate 22 via the lumbar support pad adjustment strap(s) 26, the length of the leg frame 30 may be adjusted by moving the lower leg tube 34 relative to the upper leg tube 32, and the position of the thigh foam support roller 50, the foam ankle cuff roller 60, and the footplate 70 may be adjusted to accommodate the height and/or proportion of a user.

The user's thigh 7 is then strapped to the leg stretch device 10 with a thigh retention strap 11, and the user's ankle 8 is strapped to the leg stretch device 10 with an ankle retention strap 12. It should be understood that other retentions straps may additionally or alternatively be used. For example, a foot retention strap may extend from the footplate in addition to or in substitution of the use of the ankle retention strap.

The user 1 or a clinician (not shown) manually controls the electronic controller 88 (e.g., by pressing an up button) to actuate the actuation motor 86 of the actuation assembly 80. The actuation motor 86 then drives the actuation bar 84 out of the actuation tube 82 which, in turn, raises the leg frame 30 and causes a corresponding movement of the user's foot 6 while simultaneously stretching the calf and hamstring muscles 1*a* and 1*b* of the user 1.

The user's foot 6 may be raised through a predetermined range of motion or may be raised to a stretch position and the degree of articulation measured by the degree label 46 on the hinge cover 42. The raised position may be held for a predetermined period of time, e.g., 10 seconds, 15 seconds, 20 seconds, 25 seconds, 30 seconds, etc., before the user 1 or clinician (not shown) lowers the foot 6 back to the initial position by actuation of the actuator motor 86 via the electronic controller 88. The raising and lowering of the foot 6 may be repeated a predetermined number of times, e.g., 1 time, 2 times, 3 times, 4 times, 5 times, etc., at the same or different degree angles.

In embodiments, when the foot 6 is in the raised or elevated position, the user's foot 5 may be flexed to stretch the ankle 8. For example, in the raised position, the user 1 may press the user's knee 5 down making the knee 5 straight and flexing the foot 6. This position may be held for a predetermined period of time, e.g., 5 second, 10 seconds, 15 seconds, 20 seconds, 25 seconds, 30 seconds, etc., and then may be released. This process may be repeated a predetermined number of times, for example, 1 time, 2 times, 3 times, 4 times, 5 times, etc. Additionally or alternatively, a hot pack or electrical stimulation may be applied to the user's leg 4 during elevation, and/or an ice pack may be applied to the user's leg 4 at the end of stretching.

Referring now to FIGS. 5-8, a leg stretch device 100 is shown in accordance with another embodiment of the present disclosure. Leg stretch device 100 is substantially similar to the leg stretch device 10 of FIGS. 1-4, and therefore described with respect to differences therebetween. Leg stretch device 100 includes a base frame 120 having an elongated body 120*a* terminating at proximal and distal ends 120*b* and 120*c*. The base frame 120 includes a plurality of apertures 121 spaced along the length of the base frame 120.

A support plate 122 is releasably secured to the base frame 120 via a support plate adjustment pin 123 that extends through an aperture of the plurality of apertures 121 of the base frame 120 and into a support plate bracket 122*a* that is coupled to the support plate 122 to fixedly position the support plate 122 to the base frame 120. A lower lumbar pad 124 is releasably secured to the base frame 120 via a lower lumbar pad adjustment pin 125 that extends through an aperture of the plurality of apertures 121 of the base frame 120 and into a lower lumbar support pad bracket 124*a* that is coupled to the lower lumbar pad 124 to fixedly position the lower lumbar pad 124 to the base frame 120. It should be understood that the support plate 122 and lower lumbar pad 124 are movable to any of the apertures 121 of the base frame 120 to accommodate the height and/or proportion of a user, and may extend from either side of base frame 120 to accommodate stretching of either the left or right leg of a user. Wheels 127 may be disposed at the distal end 120*c* of the base frame 120 for ease in transport of the leg stretch device 100.

A leg frame 130 is coupled to the base frame 120. The leg frame 130 includes a leg tube 132 having a unitary elongate body 132*a* terminating at proximal and distal ends 132*b* and 132*c*, respectively, and a plurality of sleeves 134, 136, and 138 that are slidably adjustable along the length of the leg tube 132. The proximal end 132*b* of the leg tube 132 is hingedly connected to the base frame 120 at hip pivot axle 140 such that the leg tube 132 is movable relative to the base frame 120 about a pivot axis defined by the hip pivot axle 140.

The hip pivot axle 140 extends through a hinge cover 142. The hinge cover 142 includes a pair of legs 143 that extends downwardly towards the base frame 120 and engages an aperture of the plurality of apertures 121 of the base frame 120. The hip pivot axle 140 is a quick release pin that may be inserted into and removed from the leg stretch device 100 to couple/uncouple the leg tube 132 from the base frame 120. The pair of legs 143 is movable to any of the apertures 121 of the base frame 120 to move the leg tube 132 proximally or distally along the longitudinal length of the base frame 120 to accommodate the height and/or proportion of a user.

A thigh support sleeve 134 is slidably engaged with the leg tube 132 and includes a first thigh support adjustment knob 134*a* for adjusting the position of the thigh support sleeve 134 along the length of the leg tube 132. A thigh foam support roller 150 is secured to the thigh support sleeve 134 by a thigh support axle 152 that extends into and through a thigh axle support hole 153 defined in a lower surface of the thigh support sleeve 134. A second thigh support adjustment knob 134*b* is engageable with the thigh support axle 152 for securing and unsecuring the thigh foam support roller 150 to and from the leg stretch device 100.

An ankle support sleeve 136 is disposed distal to the thigh support sleeve 134 and is slidably engaged with the leg tube 132. The ankle support sleeve 136 includes a first ankle support adjustment knob 136*a* for adjusting the position of the ankle support sleeve 136 along the length of the leg tube 132. A foam ankle cuff roller 160 is secured to the ankle support sleeve 136 by an ankle support axle 162 that extends into and through an ankle support hole 163 defined in a lower surface of the ankle support sleeve 136. A second ankle support adjustment knob 136*b* is engageable with the ankle support axle 162 for securing and unsecuring the foam ankle cuff roller 160 to and from the leg stretch device 100.

A foot support sleeve 138 is disposed distal to the ankle support sleeve 136 and is slidably engaged with the leg tube 132. The foot support sleeve 138 includes a first foot support adjustment knob 138*a* for adjusting the position of the foot support sleeve 138 along the length of the leg tube 132. A footplate 170 is secured to the foot support sleeve 138 by foot support axles 172 that extend into and through foot support holes 173 defined in the foot support sleeve 138. Second foot support adjustment knob 138*b* is engageable with the foot support axles 172 to securing and unsecuring the footplate 170 to and from the leg stretch device 100. The footplate 170 includes a padded surface 170*a* that is contoured to support the inner arch of a foot and allows a user to move the position of the user's foot (e.g., flexing of the foot) for stretching of the user's ankle.

It should be understood that the thigh support foam roller 150, the foam ankle cuff roller 160, and/or the footplate 170 may be any shape and size for supporting the respective parts of a user's leg, and that the leg stretch device 100 of the present disclosure may include a plurality of different sized and/or shaped thigh support foam rollers 150, foam ankle cuff rollers 160, and/or footplates 170 for interchangeable use depending on the size and needs of the user. Additionally, the thigh support foam roller 150, the foam ankle cuff roller, and/or the footplates 170 may be formed from materials other than foam, such as a shock absorbing or compressible material within the purview of those skilled in the art. The position of the thigh support foam roller 150, the foam ankle cuff roller 160, and the footplate 170 may be adjusted by sliding the respective sleeves 134, 136, and 138 along the leg tube 132, as described above, to accommodate the height and/or proportion of a user, and may be coupled to either side of the leg tube 132 for stretching of either a left leg or a right leg of a user. The first adjustment knobs 134*a*, 136*a*, and 138*a* of the sleeves 134, 136, and 138, respectively, may frictionally engage the leg tube 132 (e.g., via a threaded, spring-biased, push-pull, etc. connection) to releasably retain the sleeves 134, 136, 138 in a desired position.

An actuation assembly 180 is hingedly connected to the proximal end 120*b* of the base frame 120 via a bracket and pin assembly 181. The actuation assembly 180 includes an actuation tube 182 and an actuation bar 184 that is slidably disposed within the actuator tube 182. The actuation assembly 180 also includes an actuator motor 186 that controls the movement of the actuation bar 184 relative to the actuation tube 182. The actuator tube 182 includes a proximal end 182*a* hingedly connected to the proximal end 120*b* of the base frame 120 and the actuator bar 184 includes a distal end 184*a* hingedly connected to a bracket and pin assembly 131 extending from the leg tube 132. The bracket 131*a* of the bracket and pin assembly 131 includes a plurality of openings 131*b* in which the pin 131*c* (e.g., a quick release pin) may be disposed to change the range of motion of the leg tube 132.

The actuator motor 186 is controlled by a user or a clinician via an electronic controller 88 (FIG. 4). The electronic controller 88 is in operative communication with the actuator motor 186 such that actuation of the electronic controller 88 by the user or the clinician actuates the actuator motor 186 which, in turn, causes the actuator bar 184 to slide relative to the actuator tube 182 to push or release the leg tube 132 to change the degree angle between the base frame 120 and the leg tube 132.

In use, the position of the support plate 122, the lower lumbar pad 124, and/or the leg tube 132 may be adjusted to accommodate the height and/or proportion of a user, and the thigh foam support roller 150, the foam ankle cuff roller 160, and/or the footplate 170 may be adjusted along the length of the leg tube 132. The user then aligns his/her torso and leg with the leg stretch device 100, straps himself/herself to the leg stretch device 100, and operates the leg stretch device 100 as described above with regard to the leg stretch device 10 of FIGS. 1-4.

Referring now to FIGS. 9-12B, a leg stretch device 200 is shown in accordance with another embodiment of the present disclosure. Leg stretch device 200 is substantially similar to leg stretch devices 10, 100, and therefore described with respect to the differences therebetween. Leg stretch device 200 includes a base frame 220 having an elongated body 220*a* terminating at proximal and distal ends 220*b* and 220*c*. The base frame 220 includes a plurality of apertures 221 spaced along the length of the base frame 220.

A support plate 222 is releasably secured to the base frame 220 via a support plate adjustment pin 223 that extends through a support plate bracket 222*a* of the support plate 222 and an aperture of the plurality of apertures 221 of the base frame 220 to fixedly position the support plate 222 to the base frame 220. The support plate 222 is configured to be positioned under the thigh of a user and includes openings 225 through which a thigh strap 11 (FIG. 12A) may be secured. It should be understood that the support plate 222 may include other retaining features, such as grommets, hooks, snaps, etc., to secure a thigh strap to the support plate 222. A lower lumbar pad 224 is releasably secured to the base frame 220 via a lower lumbar support pad bracket 224*a*. It should be understood that the support plate 222 is movable to any of the apertures 221 of the base frame 220 and the lower lumbar pad 224 is repositionable along the length of the base frame 220 to accommodate the height and/or proportion of a user. The support plate 222 and lower lumbar pad 224 extend from one side of the base frame 220 and accommodates stretching of either the left or right leg of a user on the same side of the leg stretch device 200. Wheels 227 may be disposed at the distal end 220*c* of the base frame 220 for ease in transport of the leg stretch device 200 and to act as support points for increasing the stability of the leg stretch device 200.

A leg frame 230 is coupled to the base frame 220. The leg frame 230 includes an upper leg tube 232 and a lower leg tube 234 slidably coupled or telescopically mated with the upper leg tube 232. The upper leg tube 232 includes an elongated body 232*a* having a proximal end 232*b* and a distal end 232*c*. The proximal end 232*b* of the upper leg tube 232 is hingedly connected to the base frame 220 at hip pivot axle 240 such that the upper and lower leg tubes 232 and 234 move relative to the base frame 220 about a pivot axis defined by the hip pivot axle 240. The hip pivot axle 240 extends through a hinge cover 242 having a degree label 244 disposed thereon which acts as a goniometer to measure the degree of hip flexion with a straight knee during use of the leg stretch device 200.

A knee support assembly 250 is slidably adjustable along the length of the upper leg tube 232. The knee support assembly 250 includes a first knee support sleeve 252*a* disposed around the upper leg tube 232 and a leg 252b extending therefrom. A first knee support clamp 254a is disposed around the upper leg tube 232 for securing the first knee support sleeve 252a to the upper leg tube 232. A second knee support sleeve 256a is disposed around the leg 252b of the first knee support sleeve 252 and a knee support axle 256b extends therefrom. A second knee support clamp 254b is disposed around the leg 252b of the first knee support sleeve 252a for securing the second knee support sleeve 256a to the leg 252b of the first knee support sleeve 252. A knee support roller 258 is disposed around the knee support axle 256b and includes first and second contoured sections 258a and 258b configured to engage the left and right knee of a user. It should be understood, however, that the knee support roller may be a single contoured roller slidably adjustable along the length of the knee support axle 256b for engaging either the left or right knee of the user.

It should also be understood that the knee support roller 258 may be any shape and size for supporting a user's thigh or knee, and that the leg stretch device 200 of the present disclosure may include a plurality of different sized and/or shaped knee support rollers 258 for interchangeable use depending on the size and needs of the user. The position of the knee support roller 258 may be adjusted along the length of the upper leg tube 232 as well as along an axis transverse to the upper leg tube 232 to accommodate the height and/or proportion of a user and for desired placement along the user's leg.

The lower leg tube 234 includes a proximal portion 234a extending longitudinally from the upper leg tube 232 and a distal portion 234b extending substantially perpendicular to the proximal portion 234a. The proximal portion 234a of the lower leg tube 234 is received within the distal end 232c of the upper leg tube 232 for telescopic adjustment of the lower leg tube 234 relative to the upper leg tube 232. The lower leg tube 234 is manually adjustable and secured at a desired position by a telescopic clamp 236. An ankle support roller 260 is disposed over the distal portion 234b of the lower leg tube 234 such that the distal portion 234b acts as an ankle support axle. The ankle support roller 260 includes first and second contoured sections 260a and 260b configured to engage the left and right ankles of a user. It should be understood, however, that the ankle support roller may be a single contoured roller slidably adjustable along the length of the distal portion 234b of the lower leg tube 234 for engaging either the left or right ankle of the user.

It should also be understood that the ankle support roller 260 may be any shape and size for supporting a user's ankle, and that the leg stretch device 200 of the present disclosure may include a plurality of different sized and/or shaped ankle support rollers 260 for interchangeable use depending on the size and needs of the user. The position of the ankle support roller 260 may be adjusted by sliding the lower leg tube 234 relative to the upper leg tube 232, as described above, to accommodate the height and/or proportion of a user.

Footplates 270 for supporting the feet of a user are secured to the lower leg tube 234 by a pair of footplate adjustment brackets 272. The footplate adjustment brackets 272 are secured at opposed ends of the distal portion 234b of the lower leg tube 234, and a foot support axle 274, which support the footplates 270, extend through and are secured to the footplate adjustment brackets 272. The footplates 270 are rotatable about the foot support axle 274 within a range of angles, such as between about −15° (dorsiflexion) and about +35° (plantar flexion), relative to the user's leg. An ankle goniometer 275 may be secured to a bracket of the footplate plate adjustment brackets 272. The ankle goniometer 275 includes an ankle pointer 275a secured to the foot support axle 274 for measuring the degree of ankle rotation. The ankle goniometer 275 may include a pin 275b for locking the position of the footplates 270. For example, the ankle goniometer 275 may include openings 275c that are positioned a predetermined number of degrees apart from each other, such as 5°, through which the pin 275b may be disposed for fixing the angular position of the footplate 270. Additionally, a digital protractor 290 may be placed adjacent a bracket of the footplate adjustment brackets 272 to measure the degree of hip flexion with a straight knee. The footplates 270 may be slidable along the foot support axle 274 to accommodate the position of the user's foot. It should be understood that the leg stretch device 200 may include one footplate 270 that is slidable along the foot support axle 274 for supporting either the left or right foot of a user.

As shown in FIG. 11, in conjunction with FIGS. 9 and 10, an actuation assembly 280 is coupled to the base frame 220 and the upper leg tube 232 to effect articulation of the leg frame 230 relative to the base frame 220. The actuation assembly 280 includes an actuator tube 282 and an actuator bar 284 that is slidably disposed within the actuator tube 282 and controlled by an actuator motor 286. The actuation assembly 280 also includes a motor controller 281 and a power source 283, such as a rechargeable battery. The actuation assembly 280 is disposed within a housing 288 secured to the base frame 20. The actuation bar 284 extending distally through the housing 288 and includes a distal end 284a hingedly connected a bracket and pin assembly 231 extending from the upper leg tube 232. The bracket 231a of the bracket and pin assembly 231 includes opposed openings (not explicitly shown) through which the pin 231b (e.g., a quick release pin) is positioned through.

The actuator motor 286 is controlled by a user or a clinician via an electronic control 88 (FIG. 4). The electronic controller 88 is in operative communication with the actuator motor 286 such that actuation of the electronic controller 88 by the user or the clinician actuates the actuator motor 286 which, in turn, causes the actuator bar 284 to slide relative to the actuator tube 282 to push or release the leg frame 230 to change the degree angle between the base frame 220 and the leg frame 230.

As shown in FIGS. 12A and 12B, in use, a user 1 lies with the user's lower back 2 resting against the lower lumbar pad 224, the user's hip 3 aligned with the hip pivot axle 240, the user's stretched leg 4a (i.e., the leg being stretched by the leg stretch device 200) aligned with the leg frame 230, and the user's unstretched leg 4b aligned with the base frame 220. The user's thighs 7a and 7b are aligned with the support plate 222 such that the thigh 7b of the unstretched leg 4b rests upon the support plate 222. The thigh 7b of the unstretched leg 4b may be strapped to the support plate 222 via a thigh strap 11 by, for example, looping the thigh strap 11 through the openings 225 in the support plate 222, to prevent lifting of the unstretched leg 4b and rotation of the pelvis during operation of the leg stretch device 200. The front of the knee 5a (kneecap) of the stretched leg 4a rests against the knee support roller 258, the ankle 8a (heel cord) of the stretched leg 4a rests against the ankle support roller 260, and the foot 6a of the stretched leg 4a is placed against the footplate 270. The foot 6a may be strapped to the footplate 270 by a foot strap 13 which, for example, may be secured to the back of the footplate 270 by a retaining feature and looped around the foot 6a. The positioning of the front of the knee 5a against the knee support roller 258 and the ankle 6a against the ankle support roller 260 provides a better counter force at the knee 5a and helps to keep the stretched leg 4a in a straight position. Additionally, placement of the knee support roller 258 above the knee 5a prevents the unstretched leg 4b of the user 1 from interfering with and/or being crushed by the knee support roller 258 during operation of the leg stretch device 200. The leg stretch device 200 is operated as described above with regard to leg stretch devices 10, 100.

The leg stretch device 10, 100, 200 of the present disclosure may be formed of a variety of rigid material including, for example, metals, such as steel and/or aluminum, and plastics. In embodiments, the leg stretch device 10, 100, 200 or components thereof are formed from a relatively light, rigid material, such as anodized aluminum.

A number of embodiments have been described. Nevertheless, persons skilled in the art will understand the devices and methods specifically described herein and illustrated in the accompanying figures are non-limiting exemplary embodiments, and that the specification and figures should be construed merely exemplary of particular embodiments. It is to be understood, therefore, that the present disclosure is not limited to the precise embodiments described, and various other changes and modifications may be effected by persons skilled in the art without departing from the spirit and scope of the disclosure. It is also envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, those skilled in the art will envision other embodiments within the scope and spirit of the following claims.

What is claimed is:

1. A leg stretching device comprising:
   a linear base frame configured to extend along a lateral side of a user in a supine position;
   a support plate adjustably coupled to, and extending laterally from, the base frame, the support plate configured for positioning against a back side of the user;
   a lower lumbar pad adjustably coupled to, and extending laterally from, the base frame in spaced relation relative to the support plate;
   a hip pivot axle extending through a hinge cover, the hinge cover adjustably coupled to the base frame;
   a leg tube including a proximal end hingedly connected to the base frame about the hip pivot axle and a distal end;
   a foot plate operably coupled to the distal end of the leg tube; and
   an actuation assembly including an actuation tube hingedly connected to the base frame and an actuation bar slidably disposed within the actuation tube and hingedly connected to the leg tube, the actuation assembly including an actuator motor for moving the actuation bar relative to the actuation tube to reposition the leg tube relative to the base frame.

2. The leg stretching device of claim 1, further including a thigh foam support roller adjustably coupled to the leg tube.

3. The leg stretching device of claim 1, further including a foam ankle cuff roller adjustably coupled to the leg tube.

4. The leg stretching device of claim 1, wherein the hinge cover includes a degree label.

5. The leg stretching device of claim 1, wherein the leg tube includes an upper leg tube telescopically coupled with a lower leg tube such that an overall length of the leg tube is adjustable.

6. The leg stretching device of claim 1, further including an electronic controller for controlling the actuator motor of the actuation assembly.

7. The leg stretching device of claim 6, wherein the electronic controller is a handheld remote control.

8. The leg stretching device of claim 5, further including a knee support roller disposed around a knee support axle and configured to be positioned against a front of a knee of the user, the knee support axle adjustably coupled to the upper leg tube.

9. The leg stretching device of claim 5, further including an ankle support roller disposed around a distal portion of the lower leg tube in spaced relation to the foot plate, the ankle support roller configured to be positioned against a back of an ankle of the user.

10. The leg stretching device of claim 5, wherein the foot plate is supported on a foot support axle, the foot support axle secured to the lower leg tube by at least one foot plate adjustment bracket.

11. The leg stretching device of claim 1, further including a second foot plate operably coupled to the distal end of the leg tube.

12. The leg stretching device of claim 5, wherein the upper leg tube is disposed above the base frame and is moveable relative thereto along a vertical plane defined by the base frame.

13. A method of stretching a leg comprising:
   resting a back side of a user on a support plate that is adjustably coupled to, and extending laterally from, a linear base frame of a leg stretching device, the base frame extending along a lateral side of the user in a supine position;
   resting a lower back of the user against a lower lumbar pad that is adjustably coupled to, and extending laterally from, the base frame in spaced relation relative to the support plate;
   aligning a hip of the user with a hip pivot axle of the leg stretching device, the hip pivot axle extending through a hinge cover that is adjustably coupled to the base frame and hingedly connecting the base frame of the leg stretching device to a proximal end of a leg tube of the leg stretching device;
   resting a foot of the user against a footplate operably coupled to a distal end of the leg tube of the leg stretching device; and
   actuating an actuator motor of the leg stretching device to raise the leg tube and elevate the foot of the user, the actuation assembly including an actuation tube hingedly connected to the base frame and an actuation bar slidably disposed within the actuation tube and hingedly connected to the leg tube, the actuation assembly including an actuation motor for moving the actuation bar relative to the actuation tube to reposition the leg tube relative to the base frame.

14. The method of claim 13, further including resting a knee of the user against a thigh foam support roller of the leg stretching device, the thigh foam support roller being adjustably coupled to the leg tube of the leg stretching device.

15. The method of claim 13, further including resting an ankle of the user against a foam ankle cuff roller of the leg stretching device, the foam ankle cuff roller being adjustably coupled to the leg tube of the leg stretching device.

16. The method of claim 13, further including strapping at least one of a thigh, an ankle, or a foot of the user to the leg stretching device with a retention strap.

17. The method of claim 13, further including adjusting a position of at least one of the support plate or the footplate prior to actuating the actuator motor.

18. The method of claim 13, further including measuring a degree of hip flexion at the hip pivot axle.

* * * * *